(12) United States Patent
Boland

(10) Patent No.: US 10,837,961 B2
(45) Date of Patent: Nov. 17, 2020

(54) MOLECULAR IMPRINTED COLORED SILICA BEADS

(71) Applicant: Board of Regents, The University Of Texas System, Austin, TX (US)

(72) Inventor: Thomas Boland, El Paso, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 979 days.

(21) Appl. No.: 14/452,765

(22) Filed: Aug. 6, 2014

(65) Prior Publication Data
US 2015/0110833 A1   Apr. 23, 2015

Related U.S. Application Data

(60) Provisional application No. 61/892,719, filed on Oct. 18, 2013.

(51) Int. Cl.
*G01N 33/552* (2006.01)
*G01N 33/543* (2006.01)
(Continued)

(52) U.S. Cl.
CPC ......... *G01N 33/552* (2013.01); *G01N 33/545* (2013.01); *G01N 33/54313* (2013.01);
(Continued)

(58) Field of Classification Search
CPC .......... G01N 33/552; G01N 33/54313; G01N 2600/00; C08L 83/02; C08L 83/04
See application file for complete search history.

(56) References Cited

U.S. PATENT DOCUMENTS 6,251,280 B1   6/2001   Dai et al.
6,310,110 B1   10/2001   Markowitz et al.
(Continued)

FOREIGN PATENT DOCUMENTS

WO   WO 01/55095 A1   8/2001

OTHER PUBLICATIONS

Fujiki, Kazuhiro et al, "Preparatoin of a silica gel-carbon black composite by the sol-gel process in the presence of polymer-grafted carbon black", 1998, 33, 1871-1879.*
(Continued)

*Primary Examiner* — Ling Siu Choi
*Assistant Examiner* — David L Miller
(74) *Attorney, Agent, or Firm* — Norton Rose Fulbright US LLP

(57) ABSTRACT

Macromolecular imprinted silica particles ("MIP") in the presence of polymer grafted carbon black are disclosed. The disclosed molecular imprinted beads can detect disease in body fluids. For the silica gel matrix, tetraethyl orthosilicate (TEOS) was used as the backbone monomer and 3-aminopropy/triethoxysilane (APS) as a functional monomer. Carbon black was added to the sol-gel process, yielding black silica particles. Furthermore, sodium dodecyl sulfate (SDS) was used as a structure-directing agent to increase network diffusion of the template. A total of 16 MIPs were synthetized in parallel with variables that evaluate the role of key reactants in the synthesis procedure. Agglomeration tests were performed with all 16 MIPs in the presence of their template, alongside their respective controls using only phosphate buffered saline ("PBS"). Each of the MIPs was evaluated using a novel device capable of simultaneously measuring up to four samples for near infrared transmission.

3 Claims, 4 Drawing Sheets

Figure 1:
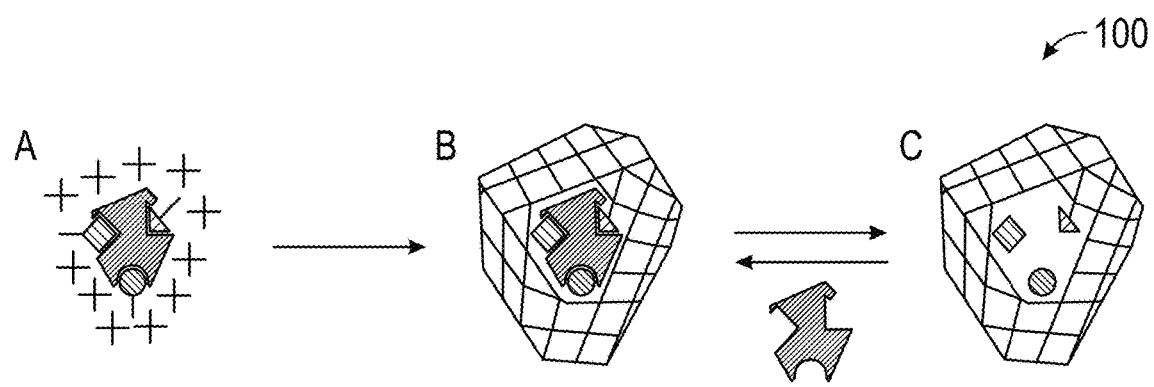
Figure 2:

(51) Int. Cl.
*G01N 33/545* (2006.01)
*G01N 33/58* (2006.01)
*A61K 39/00* (2006.01)
*C08L 83/02* (2006.01)
*C08L 83/04* (2006.01)

(52) U.S. Cl.
CPC ............ *G01N 33/585* (2013.01); *A61K 39/00* (2013.01); *C08L 83/02* (2013.01); *C08L 83/04* (2013.01); *G01N 2333/59* (2013.01); *G01N 2600/00* (2013.01)

(56) References Cited

U.S. PATENT DOCUMENTS

| | | | |
|---|---|---|---|
| 6,380,266 B1 | 4/2002 | Katz et al. | |
| 6,583,191 B2 | 6/2003 | Markowitz et al. | |
| 6,660,780 B2 | 12/2003 | Markowitz et al. | |
| 6,713,416 B2 | 3/2004 | Markowitz et al. | |
| 6,881,804 B1 | 4/2005 | Sellergren et al. | |
| 7,122,122 B2 | 10/2006 | Marquez-Sanchez et al. | |
| 7,598,087 B2 | 10/2009 | Bright | |
| 8,377,717 B2 | 2/2013 | Bright | |
| 2002/0065334 A1 | 5/2002 | Markowitz et al. | |
| 2002/0197645 A1* | 12/2002 | Martin | C12N 11/00 435/7.1 |
| 2004/0157209 A1 | 8/2004 | Yilmaz et al. | |
| 2012/0136180 A1 | 5/2012 | Roth et al. | |
| 2012/0270964 A1 | 10/2012 | Piletsky et al. | |

OTHER PUBLICATIONS

PCT International Application PCT/US2014/049929 International Search Report dated Dec. 4, 2014.

* cited by examiner

MOLECULAR IMPRINTED COLORED SILICA BEADS

CROSS-REFERENCE TO PROVISIONAL APPLICATION

This non-provisional patent application claims the benefit under 35 U.S.C. § 119(e) of U.S. Provisional Patent Application Ser. No. 61/862,719 filed on Aug. 6, 2013, entitled "MOLECULAR IMPRINTED COLORED SILICA BEADS," which is hereby incorporated by reference in its entirety.

GOVERNMENT RIGHTS STATEMENT

This invention was made with government support under 5G12MD007592-20 awarded by the National Institutes of Health. The government has certain rights in the invention.

FIELD OF THE INVENTION

The disclosed embodiments relate to imprinting polymers. The disclosed embodiments relate to molecular imprinting of high molecular weight compounds. The disclosed embodiments also relate to colored silica beads with imprinted antibody binding sites.

BACKGROUND

Molecular imprinting creates artificial receptors by the formation of a polymer network around a template molecule. Protein imprinting relates to obtaining an imprint of a protein in a polymer network. After imprinting, imprinted proteins are washed away, degraded, or digested, thus leaving behind a cavity which preferentially binds that protein. In previously proposed solutions, it has been difficult to produce imprinted microparticles from the type of polymers used. Uncolored beads used in protein imprinting are difficult to use in antibody binding assays.

Protein imprinting can be effective for molecules with low molecular weight (<1500 Da). Imprinting high molecular weight proteins or hormones, and compounds such as DNA, viruses, and bacteria within polymer matrices has been extremely challenging. For large template molecules, polymer crosslink densities seriously hinder mass transfer of the template, leading to slow template removal and rebinding kinetics or, in the worst case, permanent entrapment of the template in the polymer network due to physical immobilization. In previous proposed solutions, template rebinding is unreliably quantified, results are not evaluated critically, and often lack statistical analysis. Physicochemical properties such as charge or hydrophobicity can strongly vary in different regions of the protein template, whereas similar regions may be present in other templates. This could lead to aspecific binding and cross-reactivity of the imprinted polymer. Furthermore, the synthesis environment is usually too aggressive for the template, where the template solvent often denatures the template before an imprint is formed.

Therefore, a need exists for quantifiable imprinted molecules having a high molecular weight. The disclosed beads are utilized as diagnostics in low resource settings as no temperature control is required.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

The disclosed embodiments relate to imprinting polymers.

The disclosed embodiments relate to molecular imprinting of high molecular weight compounds.

The disclosed embodiments further relate to colored silica beads with imprinted antibody binding sites.

The above and other aspects can be achieved as is now described. A composition of a macromolecular imprinted silica particles ("MIP") in the presence of polymer grafted carbon black is disclosed. The disclosed molecular imprinted beads can detect disease in body fluids. For the silica gel matrix, tetraethyl orthosilicate ("TEOS") was used as the backbone monomer and 3aminopropy/triethoxysilane ("APS") as a functional monomer. Carbon black was added to the sol-gel process, yielding black silica particles. Furthermore, sodium dodecyl sulfate ("SOS") was used as a structure-directing agent to increase network diffusion of the template. A total of 16 MIP's were synthetized in parallel with variables that evaluate the role of key reactants in the synthesis procedure. Agglomeration tests were performed with all 16 MIP's in the presence of their template, alongside their respective controls using only phosphate buffered saline ("PBS"). Each of the MIPs was evaluated using a novel device capable of simultaneously measuring up to four samples for near infrared transmission.

Agglomeration tests were performed using carbon black, UV, fluorescent red, and silica particles synthesized without carbon black in the presence of their template. These tests were carried in parallel alongside various controls. Only carbon black silica particles agglomerated in the presence of theft template, whereas UV red and particles without carbon black settled independently regardless of presence of their template. The presence of the polymer-grafted carbon black enables the synthesis of imprinted materials that can rebind high molecular weight templates.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIG. 1 illustrates an exemplary pictorial illustration of creating artificial receptors by the formation of a polymer network around a template molecule, according to a preferred embodiment;

FIG. 2 illustrates an exemplary pictorial illustration of hCG incubated beads binding to the hCG antibody in a nitrocellulose membrane, in accordance with the disclosed embodiments;

FIG. 3 illustrates an exemplary graphical illustration of the near IR transmission through a cuvette in the presence of dispersed beads for each pair as function of time. In accordance with the disclosed embodiments;

FIG. 4A illustrates an exemplary pictorial illustration of SEM images demonstrating surface morphology, specifically black anti-WN particles at 1200×, showing microparticle shape, in accordance with the disclosed embodiments;

FIG. 4B illustrates an exemplary pictorial illustration of SEM images demonstrating surface morphology, specifically black anti-WN particles at 22,000× illustrating aggregate morphology of macroparticles, in accordance with the disclosed embodiments;

FIG. 5 illustrates an exemplary pictorial illustration of agglomeration test of UV red, carbon black, and non-colored silica particles, in accordance with the disclosed embodiments; and FIG. 6 illustrates an exemplary pictorial illustration of conical tubes containing imprinted silica particles that were re-suspended after overnight precipitation, in accordance with the disclosed embodiments.

DETAILED DESCRIPTION

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As illustrated in the exemplary pictorial illustration 100 of FIG. 1, molecular imprinting is a technique used to create artificial receptors for molecules or proteins by the formation of a polymer network around a template molecule. As shown in (A) of FIG. 1, the template, functional monomers, and crosslinker (+) form a pre-polymerization complex. In (B), polymerization of monomers and crosslinker fixes the complex. Finally, in (C), removal of the template leaves rebinding cavities.

To achieve macromolecular imprinting, the synthesis of macromolecular imprinted polymers ("MIPs") must occur at an environment where the template can maintain proper folding and 3D structures for sufficient time frames to allow the formation of the imprints. Finally, the process must allow recapturing the template for its reutilization. If new template must be used for each synthesis, the key advantages of MIPs such as scalability and cost effectiveness are eliminated; the process would be more expensive than using traditional antibodies. There are cases, however, where the availability of MIPs available as sensors or markers trump the use of antibodies, for example, in remote and low resourced settings or for defense applications.

The majority of imprinting technologies involve the synthesis and testing of MIPs in organic solvents. This is necessary as to increase hydrogen bonding interactions between template and the MIR In aqueous solutions, hydrogen bonding is reduced as well as the binding strength of non-covalent template-monomer interactions in the imprinting. A MIP that is capable of template recognition at aqueous environment is of great importance as this greatly reduces materials and skills necessary for the recognition and separation of molecules of interest.

After selecting a target template for molecular imprinting, the next step is the selection of an appropriate polymer matrix, in which high affinity binding sites can be created, ideally without introducing aspecific interactions. In the pre-polymer mixture, several possible interactions such as hydrophobic interactions, hydrogen bonds, Van der Waals forces, and electrostatic interactions determine the spatial arrangement of monomers around the protein template. This spatial arrangement is then fixed by polymerization of monomers and crosslinker. Biological macromolecules are very complex and possess many potential recognition sites at their surface, such as charged amino acids and hydrophobic hydrophilic regions. This makes the creation of molecular imprinted polymers with high selectivity challenging, due to possible cross-reactivity with proteins with similar charge or hydrophobic/hydrophilic structure as the imprinted template protein. Removal of the template leaves a chemically and sterically complementary void, or imprint, in the polymer network, which is able to rebind the template.

An important step in the process of creating imprints with high selectivity and absorption capacity is the removal of the imprinted template, especially because the imprint cavities of interest, or those cavities with the highest binding affinity, will most strongly retain the template molecules during template extraction. Moreover, diffusion and removal of high molecular weight proteins from imprinted polymers is challenging.

In the disclosed embodiments, imprints of proteins in silica microbeads are obtained from a mixture of 1.32 ml TEOS, 0.235 ml DI water, 0.33 ml of 0.1 M, and 0.4 ml of absolute ethanol, 0.33 ml of 3-aminopropyltriethoxysilane (APS) mixed with 1.5 mg of Human chorionic gonadotropin (hCG), 0.5 ml of 0.1M SDS and 0.5 ml HP black ink. The two mixtures are combined in 10 ml of water, which causes the polymerization to proceed immediately. The resulting polymers are washed, dried, ground, and separated by centrifugation. The resulting beads (1-5 microns in diameter) are washed in acetic acid/methanol (50/50) 10-20 times or until absorbance at 280 nm is below 0.04. The imprinted beads are able to rebind hCG in an antibody-based pregnancy test, such as, for example, First Response™ or EPT™.

FIG. 2 illustrates an exemplary pictorial illustration 200 of hCG incubated beads binding to the hCG antibody in a nitrocellulose membrane, in accordance with the disclosed embodiments. This is a sandwich assay, where ½ of the sandwich is the traditional antibody assay. Antibodies are more expensive than the silica beads and expire at high or low temperatures, whereas silica beads are very stable. One could also make magnetic, colored, imprinted beads using iron oxide in the formulation. These beads may be used in a flow cytometer device, as disclosed in U.S. patent application Ser. No. 13/849,124, which is incorporated by reference herein in its entirety.

Molecular imprinting utilizing sol-gel silica process in the presence of polymer grafted carbon black is disclosed. The presence of polymer-bound carbon black in a silica gel matrix improves solvent uptake. Hydrogen bonds are formed between carbonyl groups in grafted polymer and residual silanol groups in the silica gel network. Thus carbon black macromolecular imprinted silica particles are synthetized.

Since antibodies recognize target molecules by multiple weak electrostatic, hydrophobic, and hydrogen bonding interactions between the antigen binding site and the paratope of the antibody, functional monomers that mimic such interactions are needed. For the silica gel matrix, tetraethyl orthosilicate (TEOS) was used as the backbone monomer and 3-Aminopropyl triethoxysilane (APS) as a functional monomer, while carbon black and 2-pyrrolidone also have the role of potential functional monomers.

Because MIP synthesis occurs in aqueous media, water and its ionic content play an important role in the synthesis. Two water concentrations were used for each type of reaction using deionized water. The reactions were then repeated using 0.2M MES saline buffer instead of deionized water. Furthermore, it is typical for Stöber processes to be carded in water/alcohol/ammonia mixtures. Since ethanol is not essential for the current reactions, all MIPs syntheses were carried with the use of ethanol, and all reactions were repeated in the absence of ethanol in solution.

Finally sodium dodecyl sulfate (SDS) was used as a structure-directing agent, Surfactants have been used for the synthesis of mesostructured silica materials with large porosity made of uniform mesopores. The importance of mesopores in MIPs particles was seen as a way of increasing template absorption in the particle, while at the same time enhancing the template removal process and limiting permanent template encapsulation by enhancing network diffusion. To test the role of surfactants in the synthesis, all chemical reactions were carried in the presence of SOS and again repeated in the absence of such.

A total of 16 MIPs were synthetized, four variables were used: water concentration, ionic content, ethanol presence, SDS presence. Each variable had two test conditions, yielding 24 reactions. Human Chorionic Gonadotropin (hCG) was used as the template for all syntheses. After template removal and particle washing, agglomeration tests were performed with all 16 MIP's in the presence of their template, alongside their respective controls using only PBS. Each MIPs were evaluated using an in-house built device capable of simultaneously measuring up to four samples for near infrared transmission.

Experimental Procedure 2.1 Materials

Tetraethyl orthosilicate (TEOS) and 3-aminopropyl triethoxysilane (APS) were obtained from Sigma™. Human chorionic gonadotropin (hCG) was obtained lyophilized from Sigma™; a solution of 20 mg/nil was prepared in PBS buffer. Sodium dodecyl sulfate was in powder from sigma and a 10% w/v solution was prepared using ultrapure water. Hydrochloric acid (37%), ethanol, anhydrous acetic acid and methanol were acquired from Fisher Scientific™. Ammonium hydroxide was obtained from sigma at 30% concentration. Polymer grafted carbon black was obtained by collecting ink from HP™ 33 cartridges, Average sizes of this carbon black is found to be 15 nm and grafted with 2-Pyrrolidone as per MSDS, Ultrapure water was obtained from a Milli-Q Millipore unit with a water quality of at least 18.2 MΩ. 0.2M MES buffer was obtained from Fisher Scientific™ in 500 ml pouches. 1×PBS 200 ml tablets were obtained from Sigma™.

2.2. Synthesis of Imprinted Silica Particles

Imprinted silica particles were prepared by the sol-gel method. Due to the complex reaction kinetics of the silica sol-gel process, a multivariable test was performed in order to better understand the role of key reagents in the mixture. Variables for the batch process were: water content: high or low, ionic content distilled or 0.2 MES, ethanol presence: yes or no, SDS presence: yes or no. A total of 16 parallel reactions were performed.

Refinements to the order of mixtures and reagent quantities were performed. The order of reagent is paramount and if not properly followed, nucleation and gelation might occur prior to the addition of the template; hence, no molecular imprinting will occur. Furthermore, ammonium hydroxide was used as a catalyzes and APS was limited to 172 µl. In order to minimize template exposure and to increase control in reactions, two solutions were prepared. Solution one was devised to promote gelation over nucleation in solution and to introduce carbon black and SDS if present. Since solution one can be stored without reagent consumption, two such batches were prepared beforehand with and without SOS as a variable: solution 1 a was composed of 8 ml of ink, 8 ml of SDS, and 6.08 ml of ammonium hydroxide. Solution 1 b was composed of 8 ml of ink and 6.08 ml of ammonium hydroxide.

Solution two was devised to promote monomer nucleation, which occurs in a solution at or just below a pH of 4.7. Afterwards, functional monomer was added, which neutralizes the solution pH. Since a neutral pH does not favor nucleation, TEOS is allowed to hydrolyze prior to functional monomer addition, as the basicity and quantity of the monomer neutralizes the reaction's pH; TEOS hydrolysis is determined by the solution's return to room temperature. Once the solution achieves a neutral pH, the solution matches physiological conditions of the template. For our particular batch, pH was left as is on all solutions and HCG template was added.

Since all 16 reactions were synthesized in parallel of each other, individual solutions were prepared. In order to simplify the batch process, solutions 2 were grouped as follows:

TABLE 1

Group 1

| Solution | Water Quantity | Ionic content | Alcohol | SDS |
|---|---|---|---|---|
| 2A | Low | Deionized | YES | YES* |
| 2B | Low | Deionized | YES | NO† |
| 2C | Low | Deionized | NO | YES* |
| 2D | Low | Deionized | NO | NO† |

TABLE 2

Group 2

| Solution | Water Quantity | Ionic content | Alcohol | SDS |
|---|---|---|---|---|
| 2E | Low | 0.2M MES | YES | YES* |
| 2F | Low | 0.2M MES | YES | NO† |
| 2G | Low | 0.2M MES | NO | YES* |
| 2H | Low | 0.2M MES | NO | NO† |

TABLE 3

Group 3

| Solution | Water Quantity | Ionic content | Alcohol | SDS |
| --- | --- | --- | --- | --- |
| 2I | High | Deionized | YES | YES* |
| 2J | High | Deionized | YES | NO† |
| 2K | High | Deionized | NO | YES* |
| 2L | High | Deionized | NO | NO† |

TABLE 4

Group 4

| Solution | Water Quantity | Ionic content | Alcohol | SDS |
| --- | --- | --- | --- | --- |
| 2M | High | 0.2M MES | YES | YES* |
| 2N | High | 0.2M MES | YES | NO† |
| 2O | High | 0.2M MES | NO | YES* |
| 2P | High | 0.2M MES | NO | NO† |

Synthesis of Group 1

Solutions 2A-2D have two common variables, despite of this, each solution was prepared individually. Briefly, these solutions were prepared using 1.5 ml of deionized water each. For solutions 2A and 2B, 820 µl of ethanol was added, respectively. Then 6 µl of HCl was added to all solutions. All solutions were gently agitated by hand; reactions were then allowed to return to room temperature before any further reagent addition. Afterwards, 35 µl of APS was added, followed by 25 µl of HCl. It is at this stage where pH should be neutral as determined by prior experimentation.

Afterwards, 65 µl of hCG template was added. A short amount of time is allowed for template adsorption at nucleating sites of the silica sol; solutions are gently agitated by hand during this process. Finally, 135 µl of APS was added followed by the appropriate solution one; for solutions 2A and 2C, solution 1a was used; and for solutions 2B and 2D, solution 1b was used. All solutions were topped off by adding of 40 ml of deionized water.

Synthesis of Group 2

Solutions 2E-2H were synthesized as 2A-2C with the exception of using 0.2 M MES rather than deionized water.

Synthesis of Group 3

Solutions 2I-2L prepared using 2.4 ml of deionized water each. For solutions 2I and 2J, 820 µl of ethanol was added followed by 6 µl of HCl. Ail solutions were gently agitated by hand; reactions were then allowed to return to room temperature before any further reagent addition. Afterwards, 56 µl of APS was added, followed by 25 µl of HCl. Afterwards, 100 µl of hCG template was added. A short amount of time is allowed for template adsorption at nucleating sites of the silica sol; solutions are gently agitated by hand during this process. Finally, 115 µl of APS was added followed by the appropriate solution one; for solutions 2I and 2K solution 1a and solutions 2J and 2L solution 1b was used.

Synthesis of Group 4

Solutions 2M-2P were prepared as 2I-2L with the exception of using 0.2 M MES buffer instead of deionized water.

2.6. Template Removal

To remove unreacted monomers, resulting molecular imprinted particles were centrifuged at 4000 RPM for 10 minutes, rinsed with 40 ml of deionized water in triplicate. In previous papers, imprinted particles were allowed to dry and grinded against a stainless steel mortar until large agglomerates were no longer observed. This was not done because the carbon black limits the aggregate size and prevents large agglomerations and most of the imprints are located at the surface of the particles. In short, particle grinding is not necessary for particles that are easily suspended in water and remain colloidal for longer than 5 minutes.

After triplicate rinsing, particles were washed in 40 ml of elution solution consisting of 50% v/v mixture of glacial acetic acid and methanol at room temperature under sonication for 10 minutes. Particles were then centrifuged at 4000 RPM for 10 minutes, 2 ml of supernatant was collected per solution. Particles were then rinsed in triplicate with 40 ml of deionized water. Absorbance of the elution supernatant was measured by uv-vis spectrometry at 280 nm. If absorbance was measured in the supernatant, this indicated unbinding of the template. If absorbance values were larger than 0.040, solutions were washed again in 40 ml of elution solution and rinsed in triplicate. Finally, particles were centrifuged at 4000 RPM for 10 minutes and suspended in a 1×PBS solution and stored at room temperature until needed. Particle concentrations were found to be at 58±18 mg/ml.

Synthesis of Sol-Gel Affinity Columns 2.7. Materials

Tetraethyl orthosilicate (TEOS) and 3-Aminopropyl triethoxysilane (APS) were obtained from Sigma and used as is. Hydrochloric acid (37%), ethanol, and methanol were acquired from Fisher Scientific®. Anhydrous acetic acid was also from Fisher Scientific. Polymer grafted carbon black was obtained by collecting ink from HP 33 cartridges. According to literature, carbon black are 15 nm carbon particles [7] grafted with 2-Pyrrolidone as per HP MSDS. Ultrapure water was obtained from a Milli-Q Millipore unit with a water quality of at least 18.2 MΩ. 0.1M MES buffer was obtained as powder pouches from Fisher Scientific®. 1×PBS 200 ml tablets were obtained from Sigma®. Elution buffer was made with 0.15 M NaCl and 0.5% acetic acid. West Nile antibodies (AWN) where obtained from mouse ascitic fluid. Antibodies where purified by antibody affinity gel goat affinity purified antibody to mouse IgG column from MP bio #55581. Resulting antibody is then desalted with GE Hitrap 5 ml desalting column. Biomate 3 UV-Vis spectrophotometer was used for protein determination with BCA and micro BCA kits from Fisher Scientific®. Tricorn 10/50 column #28-4064-14 was used for HPLC testing. Pierce Centrifuge columns #89896 where used as chromatography columns for MIPs synthesized. HPLC UNIT 2.8. Synthesis of Imprinted Silica Particles Imprinted silica particles were prepared by the sol-gel method. In order to maximize particle retention, a two-step synthesis protocol was devised. The main protocol focuses on molecular imprinting which produces a broad range of molecular imprinted particles in the nanometer scale. In order to contain these, a silica gel is produced where the particles are suspended and trapped in a silica gel matrix resulting in fewer particle losses during washing and regeneration protocols. The order of reagents is of utmost importance and if not properly followed, nucleation and gelation might occur prior to the addition of the template, thus reducing or inhibiting molecular imprinting. It is noted that all disclosed reactions are scalable.

For the synthesis of MIPs: 365 µl of 2×MES was added to a 1.5 ml conical centrifuge tube, followed by 146 µl of TEOS, then 11.8 µl of HCl, afterwards 45 µl of APS and 11.3 µl of cAPS applied by vigorously pipetting, then 222 µl of AWN with a concentration of 100 µg/ml, followed by 62.5

μl of ink, solution was mixed by vigorously pipetting the solution for at least 30 seconds. Afterwards, solution is left overnight.

For MIP particle encapsulation: 487 μl of TEOS is added to a 5 ml glass tube, MIP particles are resuspended in solution and the entire contents are added to the glass tube, 97.3 μl of APS and 24.3 μl of cAPS are then added and mixed by pipetting vigorously, followed by 208 μl of ink, and finally 684 μl of ethanol are added. After an hour, the solution becomes a gel which is then transferred to a HPLC column or a centrifuge column depending on test.

Particles were loaded to an HPLC column for non-specificity and protein retention testing. This was accomplished by transferring gel during curing time before the gelation point or after gelation by resuspending gel in 1 ml of 2×PBS and pipetting the gel to the column. A total of 3 MIP columns and 3 non-imprinted (NIP) columns were created. Column packing was achieved by monitoring column backpressure to no more than 150 psi. Depending on batch, flow rates varied from 0.6 ml/min to 1 ml/min. If backpressure was exceeded for extended periods, column clogged and repacking was necessary.

After column packing, MIP columns were equilibrated with 2×PBS until absorbance at 280 nm stabilized. Afterwards, 20 μl of AWN serum was injected through the sample injector. After column equilibration, buffer was changed to elution buffer in order to elute retained antibody from the column. In case of protein detection, sample was collected immediately from the detector's output. For NIP columns, no protein was detected during protein elution; therefore, samples were not collected. All samples from MIP columns collected were processed with a desalting column for buffer exchange to 1×PBS buffer. Mouse ascitic fluid, purified antibody from the affinity column, and collected samples were then tested with a western blot.

For antibody activity, particles were loaded to centrifuge columns by transferring MIP gel after suspending in 1 ml 2×PBS. A total of X MIP columns and Y NIP columns were fabricated. Each column was loaded with 800 μl of gel and 4 ml of elution buffer. Columns were then centrifuged at 180 g's for 5 minutes. Compacted gel was resuspended with remaining solution with a vortex. Columns were centrifuged and steps were repeated until columns were free of solution. A total of 12 ml of elution buffer was used; no protein was detected in final elution with micro BCA kit. Columns were then stabilized with 6 ml of 2×PBS in the same manner as before.

For column testing, 60 μl of AWN serum was added to columns along with 800 μl of 2×PBS. Gel was resuspended with a vortex and columns were incubated for 3 hours. After incubation, columns were centrifuged for 5 minutes at 180 g's, eluent was discarded. Column was then washed with X ml of 2×PBS to remove nonspecific bound molecules. To elute antibody from the column, 800 μl of elution buffer was added. Gel was resupended, centrifuged, and sample was collected. Elution step was repeated and both elution samples were added. Afterwards, samples were then changed to 1×PBS buffer solution with a desalting column. Up to 500 μl of the samples were tested for protein with BCA and micro BOA kits depending on protein concentration. Samples were also tested with ELISA for antibody activity and concentration.

3. Results

After synthesis of all MIP, data was obtained as explained below.

3.1. Imprinted Particles Color Intensity

After template removal, black color intensity was observed different from groups 1 and 2 when compared against groups 3 and 4. In order to quantify color intensity, images were recorded and black saturation percentage measured using Adobe™ Photoshop™ CS5.1. Results are summarized in Table 5.

TABLE 5

Black Color Intensity

| Particles | Group 1 Color % | Group 2 Color % | Group 3 Color % | Group 4 Color % |
| --- | --- | --- | --- | --- |
| A\|E\|I\|M | 95 | 95 | 80 | 90 |
| B\|F\|J\|N | 95 | 95 | 80 | 85 |
| C\|G\|K\|O | 95 | 95 | 90 | 85 |
| D\|H\|L\|P | 95 | 95 | 80 | 85 |

3.2. Reagent Retention and Template Removal

During template removal process, batch groups 1 and 2 where particularly difficult to process. These set of particles better retained reagents and SDS as well. Because of this, group 1 and 2 particles required an extra washing procedure when compared to groups 3 and 4. These samples also showed darker color intensity. Thus, we conclude that higher carbon black concentrations enhances solvent uptake, but at the same time this suppresses washing effectiveness probably by increasing network crosslinking.

In addition of being required for molecular imprinting, excessive concentrations of polymer grafted carbon black will slow the gelation process which is necessary for molecular imprinting to occur. Thus, we conclude that there is a best concentration range of carbon black approximately between 0.5% and 1.5%. This is because carbon black must render enough material to assist in molecular imprinting while at the same time the effect of reagent uptake and the suppression of the gelation process must be limited.

3.4. Rate of Precipitation

In order to quantify precipitation rates, a device was built with 4 sensors capable of reading infrared transmission changes per time in a standard disposable cuvette. The device is capable of collecting changes from full dispersion up to almost full precipitation with a resolution of 1024 bits. The device was programed to collect values of all sensors simultaneously every 2 seconds and values where recorded and transferred to a spread sheet for processing and evaluation.

For rate of precipitation tests, 2 mg of all batch particles where collected in solutions individually. Then 400 μg of hCG was added to each. Finally the solutions where suspended in a total volume of 3 ml in 1×PBS solution. The same process was repeated, but with the absence of hCG as a control value of rate of precipitation per solution. Tests were performed in pairs of solutions with their respective template and control per particle type.

Figure 3:
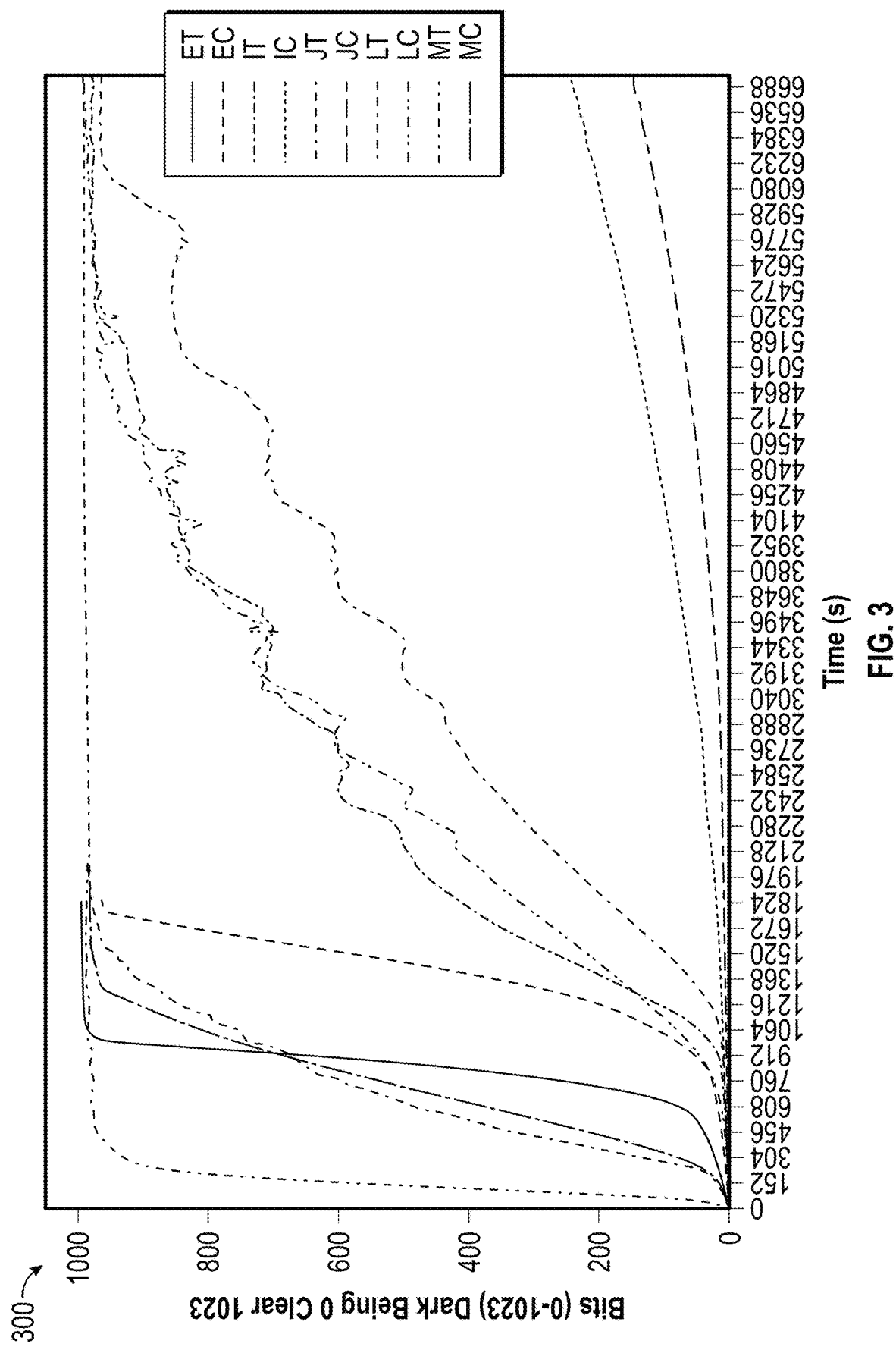
Figure 4A:
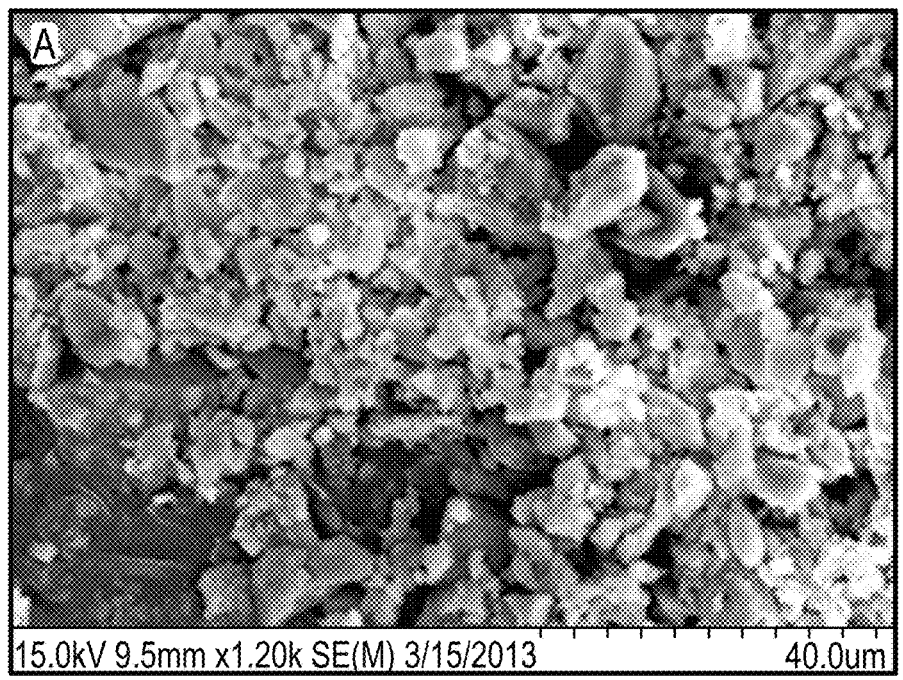
Figure 4B:
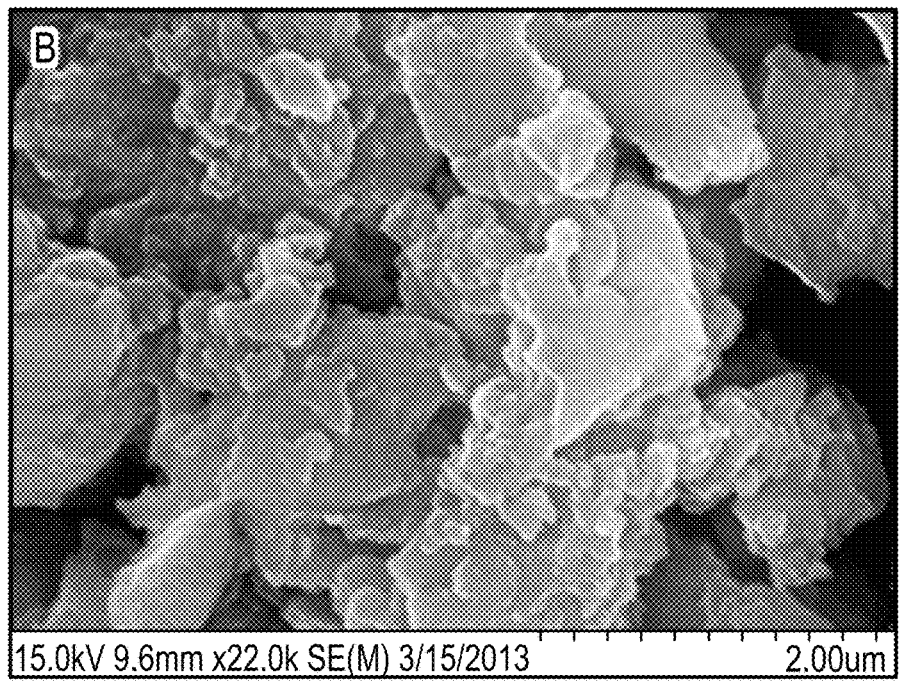
Figure 5:
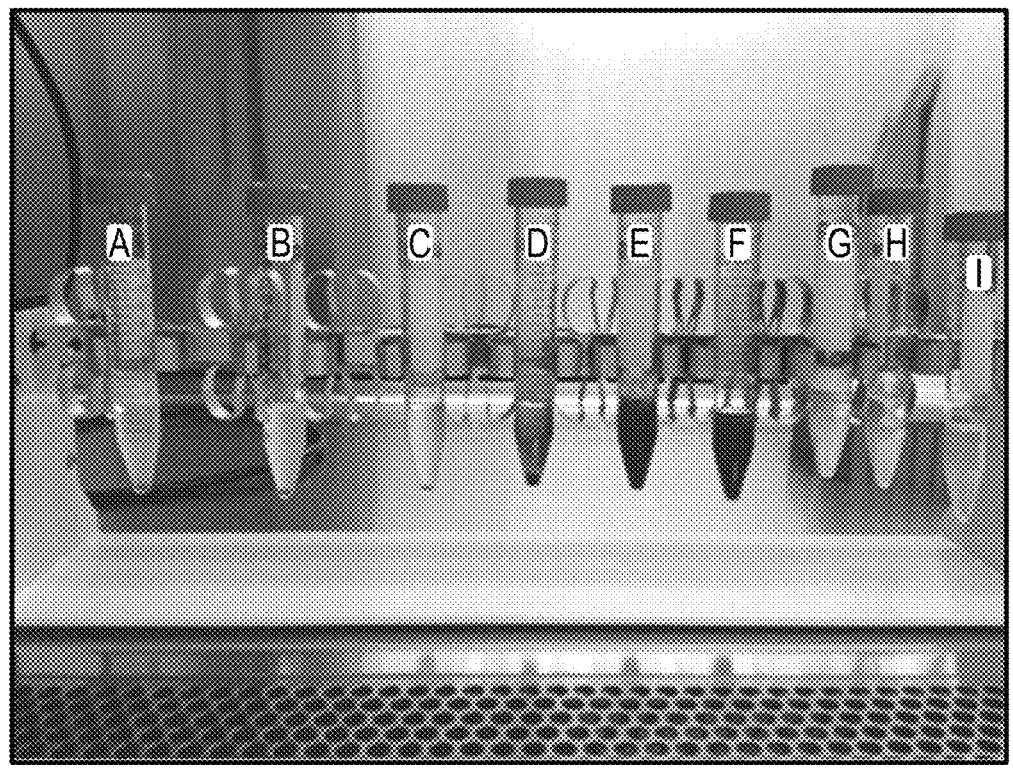
Figure 6:
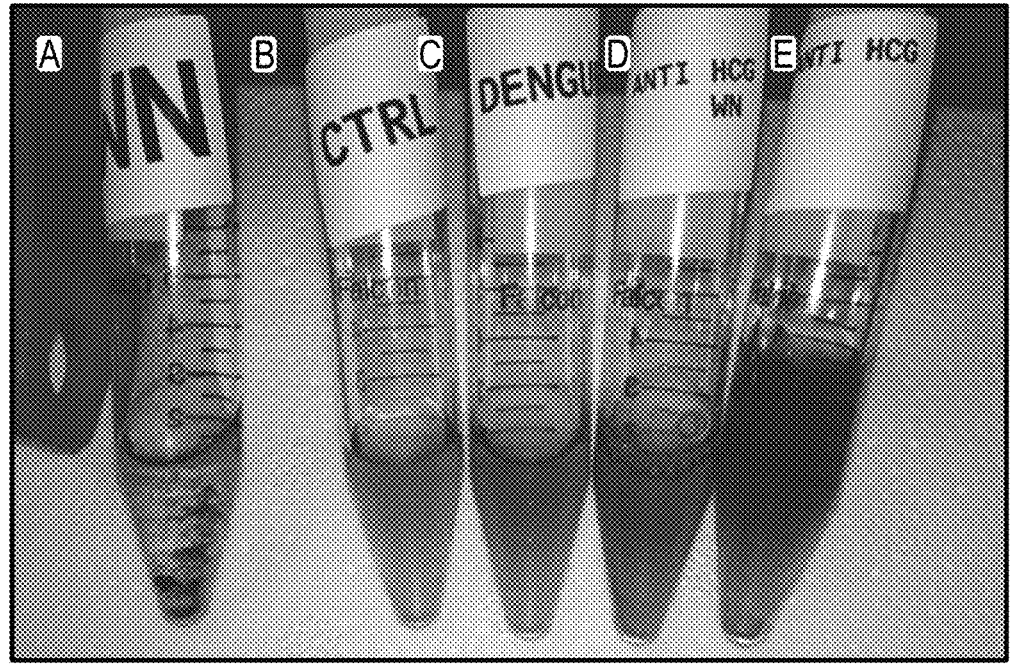

FIG. 3 illustrates an exemplary graphical illustration 300 of the near IR transmission through a cuvette in the presence of dispersed beads for each pair as function of time, in accordance with the disclosed embodiments. As can be seen from the figure, all solutions block nearly all transmission initially, but become more transparent as the particles settle due to gravity and agglomeration. The rate of precipitation is determined by the slope of the curves. As each batch will have a slightly different precipitation rate, the ratio of the rates when hCG was added to the rates in solvent alone were calculated. A successful imprint was determined if a ratio equal or greater than 2 was observed, meaning that the rate of precipitation for the template containing solution must be at least twice as fast as the rate of precipitation of its own control.

Table 6 summarizes the precipitation rates for 16 samples.

TABLE 6

Ratio of Template Over Control Decay Slopes.

| Particles | Group 1 Ratio | Group 2 Ratio | Group 3 Ratio | Group 4 Ratio |
|---|---|---|---|---|
| A\|E\|I\|M | 1 | 2 | 4.15 | 5.08 |
| B\|F\|J\|N | 1 | 1 | 4.22 | 1 |
| C\|G\|K\|O | 1 | 1 | 1 | 1 |
| D\|H\|L\|P | 1 | 1 | 2.83 | N/A |

N/A: Estimated values from prior observations. Particles were not available for testing with device.

For group 1, there was no successful imprinting in any of the particles A to D. In group 2, only particles 2E were successful in rebinding their template, but had the smallest slope ratio of all other successful imprints. In group 3, particles 2I, 2I and 2L would rebind their target, whereas 3L had the least slope ratio from the group and second smallest from the batch. In group 4, particles 2M and 2P rebound to their template and particles 2M showed the greatest measured slope ratio from all other particles in the batch. Even though particles 2P were not measured by the device as the particles were exhausted prior to the device being ready for use, prior observational experiments would point to a very high ratio of precipitation slopes, 3.4. Discussion From FIG. 3, it can be seen that groups 3 and 4 precipitated faster than particles in group 2. These results are in agreement with the previous reasoning that an optimal carbon black ratio must be found in order to achieve good rebinding and good particle dispersion. If control particles remain for an indefinite amount of time under dispersion, then it will be difficult to achieve precipitation of template loaded particles since dispersion is widely favored by the 2-Pyrrolidone.

Particles produced in the presence of SDS and ethanol yielded a total of 3 out of 4 successful imprints, whereas particles produced in the absence of SDS and ethanol produced a total of 2 out 4 successful imprints. For particles produced in the presence of ethanol and the absence of SDS, only particle J imprinted successfully. No particles where successfully imprinted for those in the presence of SDS and the absence of ethanol.

Based on these observations, it is clear that SDS is not a required reagent as thought of before, but it does play a role in the reaction increasing the chance of a successful imprint. It is then believed that an optimal SDS quantity must be used for templates that are able to tolerate low doses of SOS, whereas if a delicate template is used SDS could be avoided. The role of ethanol is yet unclear, it seems to be more important when SOS is also used, and potentially it acts as a dispersant of SDS.

Water content was found to be particularly important for the material yield of the synthesis, where group 1 and 2 had the least material and group 3 and 4 produced the most material. Furthermore, ionic content role was found more difficult to interpret since deionized water produced the same amount of successful imprints as those produced in 0.2 MES. Despite of this, 0.2 MES is believed to be the best alternative as 2 of its 3 successful imprints produced the largest slope ratios from the batch. Furthermore, all particles produced under 0.2 MES produced straight slopes whereas particles produced with deionized water had steps in each of the template containing solutions with successful imprinted particles.

Finally, a new imprinting method is proposed for this particular sol-gel process, where molecular imprinting occurs at the gelation process and not in the nucleation of the monomers; hence, produced MIPs are not bulk particles but rather a new type of MIP were template imprinting occurs at the aggregation sites between primary particles. This imprinting method could be thought of as a new type of surface imprinting.

4. Conclusions

The effect of water, quantity, ionic content, SOS, and ethanol in the reaction environment to synthesize of molecularly imprinted particles was investigated. The ability of the MIPs to rebind their target was evaluated by measuring sedimentation rates. While no clear rules can be derived yet, the amount of water is critical, the amount of carbon black should be below 1.5%, both SDS and alcohol should either be present together or absent, and it is preferable to use MEP over deionized water. Resulting MIPs are surface imprinted and can rebind their target. Under the best reaction conditions tested to date, the MIPs will precipitate by a factor of 5 times faster in the presence of their template that without it. When sealed from the environment, the MIPs are stable for months, which may make them very attractive for use as sensors or vaccines in low resource or defense applications.

| | MIPs |
|---|---|
| Affinity | $10^{-3}$-$10^{-10}$ M |
| Application | Organic or aqueous media |
| Capacity | ~0.1-10 μmol/g |
| Cost | $10's for g quantities |
| Production | 2-3 days |
| Reusability | 100's of times |
| Stability | Wide temperature and pH range |
| Storage time | Stable over period of years |

FIG. 4A illustrates an exemplary pictorial illustration 400 of SEM images demonstrating surface morphology, specifically black anti-WN particles at 1200×, showing macroparticle shape, in accordance with the disclosed embodiments. FIG. 4B illustrates an exemplary pictorial illustration 450 of SEM images demonstrating surface morphology, specifically black anti-WN particles at 22,000× illustrating aggregate morphology of macroparticles, in accordance with the disclosed embodiments.

FIG. 5 illustrates an exemplary pictorial illustration 500 of agglomeration test of UV red, carbon black, and non-colored silica particles, in accordance with the disclosed embodiments. A, D, G samples are UV red, carbon black, and non-colored silica particles in the presence of anti-WN template respectively. B, E, H samples are UV red, carbon black, and non-colored silica particles in the presence of HCG as a false positive control. C, F, I samples are UV red, carbon black, and non-colored silica particles in PBS as standard control.

FIG. 6 illustrates an exemplary pictorial illustration 600 of conical tubes containing imprinted silica particles that were re-suspended after overnight precipitation, in accordance with the disclosed embodiments. In FIG. 6: (A) indicates anti-West Nile imprinted silica particles in presence of mouse anti-WN antibody containing serum; (B) indicates anti-WN beads in PBS; (C) indicates WNP in presence of mouse anti-Dengue antibody containing serum; (D) indicates hCG imprinted silica particles in presence of mouse anti-WN antibody containing serum; and (E) indicates hCG imprinted silica particles in PBS.

Based on the foregoing, it can be appreciated that a number of different embodiments, preferred and alternative are disclosed herein. For example, in one embodiment, a method of imprinting silica beads can be implemented. The method can include adding polymerized silica, a precursor, and carbon black in a presence of a molecular template; polymerizing the polymerized silica, the precursor, and the carbon black around the molecular template and forming a polymerized matrix bead; and washing the molecular template out of the polymerized matrix bead, wherein an imprint of the precursor remains in the polymerized matrix bead as an imprinted matrix space.

In some embodiments, the silica comprises macromolecular imprinted silica particles. In other embodiments, the precursor comprises at least one of an antibody, a virus, a protein, a hormone, an antigen, an enzyme, a molecule, a molecule with a molecular weight less than or equal to 1500 Da, and a molecule with a molecular weight greater than 1500 Da. In other embodiments, the molecular template leaves a chemically and sterically complementary void or imprint in the polymerized matrix bead, wherein the void rebinds the molecular template. In yet another embodiment, a step can be implemented for utilizing a silica gel matrix and tetraethyl orthosilicate as a backbone monomer and 3-aminopropy/triethoxysilane as a functional monomer, wherein the imprinted silica particles are prepared utilizing sol-gel affinity columns, further comprising utilizing sodium dodecyl sulfate (SDS) as a structure-directing agent by forming mesopores that increase template absorption, enhance molecular template removal, and limit permanent template encapsulation by enhancing network diffusion.

In other embodiments, a step can be implemented for imprinting the precursor in the polymerized matrix bead and forming a colored polymer bead of a preferred diameter range measuring from 1 micron to 8 microns. In another embodiment, a step can be implemented for synthesizing imprinted materials in a presence of polymer-grafted carbon black, wherein the imprinted materials rebind high molecular weight templates. In yet another embodiment, a step can be implemented for injecting the imprinted polymerized matrix bead into a living specimen and the living specimen selectively producing antibodies that fill the imprinted matrix space, thus creating a vaccine.

In yet another embodiment, an imprinted silica bead is disclosed. The imprinted silica bead can include polymerized silica, a precursor, and carbon black in a presence of a molecular template, wherein an imprint of the precursor remains in the polymerized matrix bead as an imprinted matrix space. In an embodiment, the silica comprises macromolecular imprinted silica particles. In yet another embodiment, the precursor comprises at least one of an antibody, a virus, a protein, a hormone, an antigen, an enzyme, a molecule, a molecule with a molecular weight less than or equal to 1500 Da, and a molecule with a molecular weight greater than 1500 Da. In other embodiments, the molecular template comprises a chemically and sterically complementary void or Imprint in the polymerized matrix bead, wherein the void is capable of rebinding the molecular template. In an embodiment, the precursor is imprinted in the polymerized matrix bead. In yet other embodiments, the colored polymer bead has a preferred diameter range measuring from 1 micron to 8 microns.

In another embodiment, an imprinted silica microbead is disclosed. The imprinted silica microbead can include polymerized silica; a molecule with a high molecular weight imprinted in a location of the polymerized silica; and an artificial receptor at the location of the imprinted molecule, wherein the artificial receptor selectively binds molecules. In an embodiment, the silica comprises macromolecular imprinted silica particles. In yet other embodiments, the precursor comprises at least one of an antibody, a virus, a protein, a hormone, an antigen, an enzyme, a molecule, a molecule with a molecular weight less than or equal to 1500 Da, and a molecule with a molecular weight greater than 1500 Da. In other embodiments, the molecular template comprises a chemically and sterically complementary void or imprint in the polymerized matrix bead, wherein the void is capable of rebinding the molecular template. In yet another embodiment, the precursor is imprinted in the polymerized matrix bead. In an embodiment, the colored polymer bead has a preferred diameter range measuring from 1 micron to 8 microns.

It will be appreciated that variations of the above-disclosed and other features and functions, or alternatives thereof, may be desirably combined into many other different systems or applications. Furthermore, various presently unforeseen or unanticipated alternatives, modifications, variations or improvements therein may be subsequently made by those skilled in the art which are also intended to be encompassed by the following claims.

What is claimed is:

1. An imprinted silica composition, comprising:
a polymerized silica particle having 0.5 to 1.5 wt. % polymer-grafted carbon black, the polymer-grafted carbon black comprises a polymer and a carbon black,
wherein the polymerized silica particle comprises an imprinted binding site for binding of a macromolecule, wherein at least a portion of the binding site is formed by the polymer and the carbon black, and the polymer and the carbon black is configured to interact with the macromolecule by electrostatic, hydrophobic, and/or hydrogen bonding interactions,
and wherein the polymerized silica particle is obtained by polymerizing tetraethyl orthosilicate (TEOS), 3-aminopropyltriethoxysilane (APS), and the polymer-grafted carbon black around the macromolecule to form a macromolecule bound imprinted silica composition, and washing said macromolecule out of the macromolecule bound imprinted silica composition, wherein an imprint of said macromolecule remains in said polymerized silica particle.

2. The imprinted silica composition of claim 1 wherein said macromolecule is an antibody, a virus, a protein, a hormone, an antigen, an enzyme, or a molecule with a molecular weight greater than 1500 Da.

3. The imprinted silica composition of claim 1 wherein the polymerized silica particle has a diameter from 1 micron to 8 microns.

* * * * *